US009540258B2

(12) United States Patent
Laaroussi et al.

(10) Patent No.: US 9,540,258 B2
(45) Date of Patent: Jan. 10, 2017

(54) APPARATUS AND METHOD FOR HARVESTING AND DEWATERING OF MICROALGAE BIOMASS

(71) Applicant: E2METRIX INC., Sherbrooke, Quebec (CA)

(72) Inventors: Mohamed Laaroussi, Orford (CA); Ihsen Ben Salah, Sherbrooke (CA); Mathieu Filion, Sherbrooke (CA); Abderrazak Berrak, Sherbrooke (CA)

(73) Assignee: E2METRIX INC. (CA)

( * ) Notice: Subject to any disclaimer, the term of this patent is extended or adjusted under 35 U.S.C. 154(b) by 0 days.

(21) Appl. No.: 14/432,335

(22) PCT Filed: Sep. 30, 2013

(86) PCT No.: PCT/CA2013/000828
§ 371 (c)(1),
(2) Date: Mar. 30, 2015

(87) PCT Pub. No.: WO2014/047726
PCT Pub. Date: Apr. 3, 2014

(65) Prior Publication Data
US 2015/0251932 A1  Sep. 10, 2015

Related U.S. Application Data

(60) Provisional application No. 61/706,917, filed on Sep. 28, 2012.

(51) Int. Cl.
C02F 1/46 (2006.01)
C02F 1/463 (2006.01)
(Continued)

(52) U.S. Cl.
CPC ........... *C02F 1/463* (2013.01); *C02F 1/46104* (2013.01); *C12M 21/02* (2013.01); *C12M 33/00* (2013.01);
(Continued)

(58) Field of Classification Search
CPC ..... C02F 1/463; C02F 1/465; C02F 2201/461; C02F 2001/46119; C02F 2301/024; C02F 2201/4611; C12M 47/02
See application file for complete search history.

(56) References Cited

U.S. PATENT DOCUMENTS

2003/0173300 A1* 9/2003 Bradley ............. B01D 17/0217
210/665
2013/0228464 A1* 9/2013 Eckelberry ............. A01G 33/00
204/573

* cited by examiner

*Primary Examiner* — Arun S Phasge
(74) *Attorney, Agent, or Firm* — Brouillette and Partners; Damien Calvet

(57) ABSTRACT

An apparatus and method for separating, harvesting and primary dewatering microalgae biomass from a microalgae solution by destabilization thereof with addition of kinetic energy thereto is disclosed. The method to overcome the energetic barrier preventing a fluid-solid separation comprises injecting the microalgae solution in an electrolytic system comprising an electrocoagulation reactor generally comprising an anode module and a cathode module, the anodes and the cathode(s) being adapted to be electrically connected to perform electrolysis, thus separating, harvesting and primary dewatering microalgae biomass. Such process is generally achieved by providing a DC electric current, between the anodes and the cathode(s), to perform the separation of the biomass in the solution, in preparation the following process steps of for liquid/solid separation and primary dewatering.

14 Claims, 9 Drawing Sheets

(51) Int. Cl.
  *C12M 1/00*   (2006.01)
  *C12M 1/26*   (2006.01)
  *C02F 1/465*   (2006.01)
  *C02F 11/12*   (2006.01)
  *C02F 1/00*   (2006.01)
  *C02F 1/461*   (2006.01)

(52) U.S. Cl.
  CPC ............... *C12M 47/14* (2013.01); *C02F 1/465* (2013.01); *C02F 11/127* (2013.01); *C02F 2001/007* (2013.01); *C02F 2001/46119* (2013.01); *C02F 2001/46133* (2013.01); *C02F 2201/006* (2013.01); *C02F 2201/461* (2013.01); *C02F 2201/4611* (2013.01); *C02F 2201/4613* (2013.01); *C02F 2301/022* (2013.01); *C02F 2301/024* (2013.01)

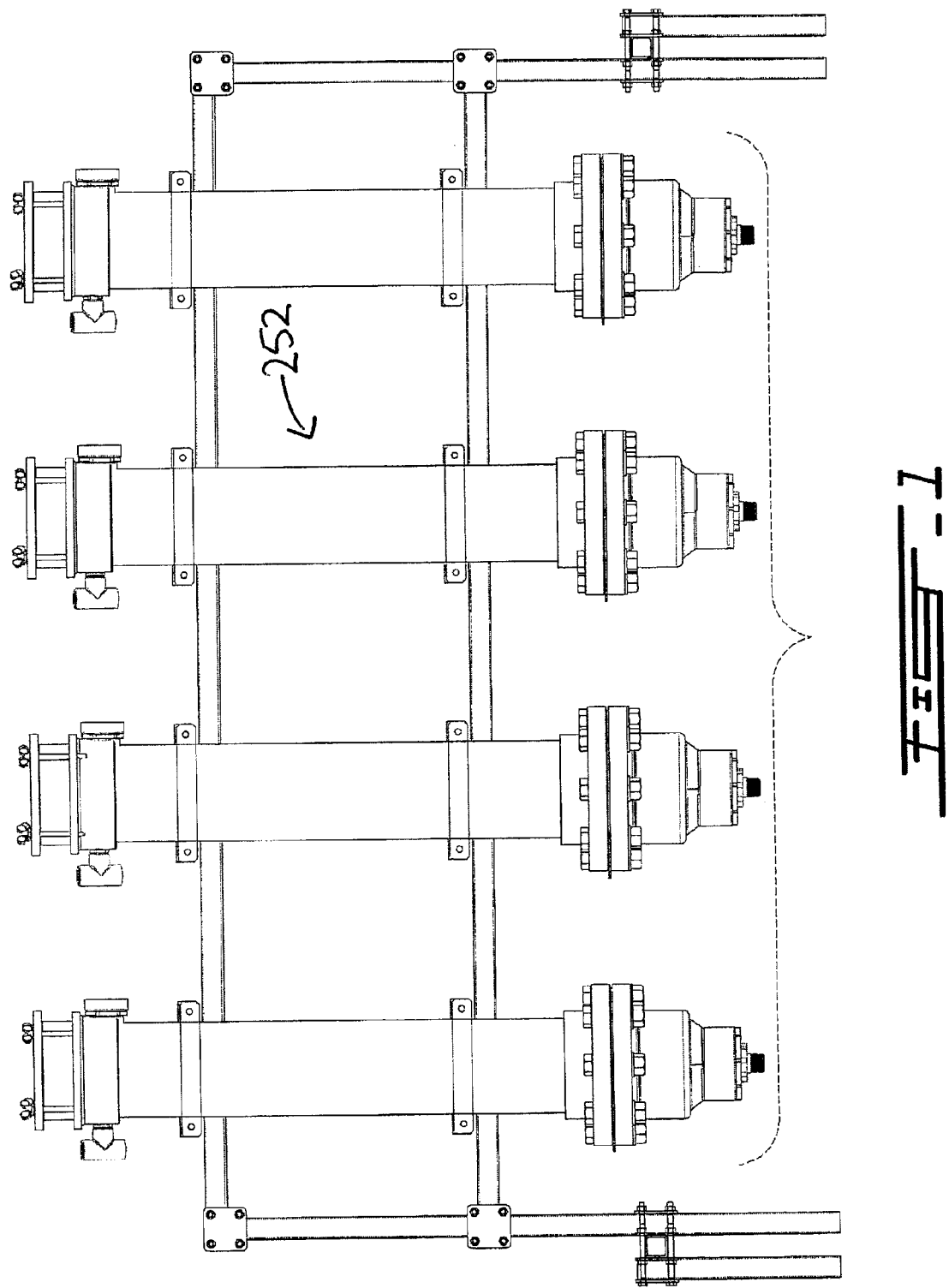

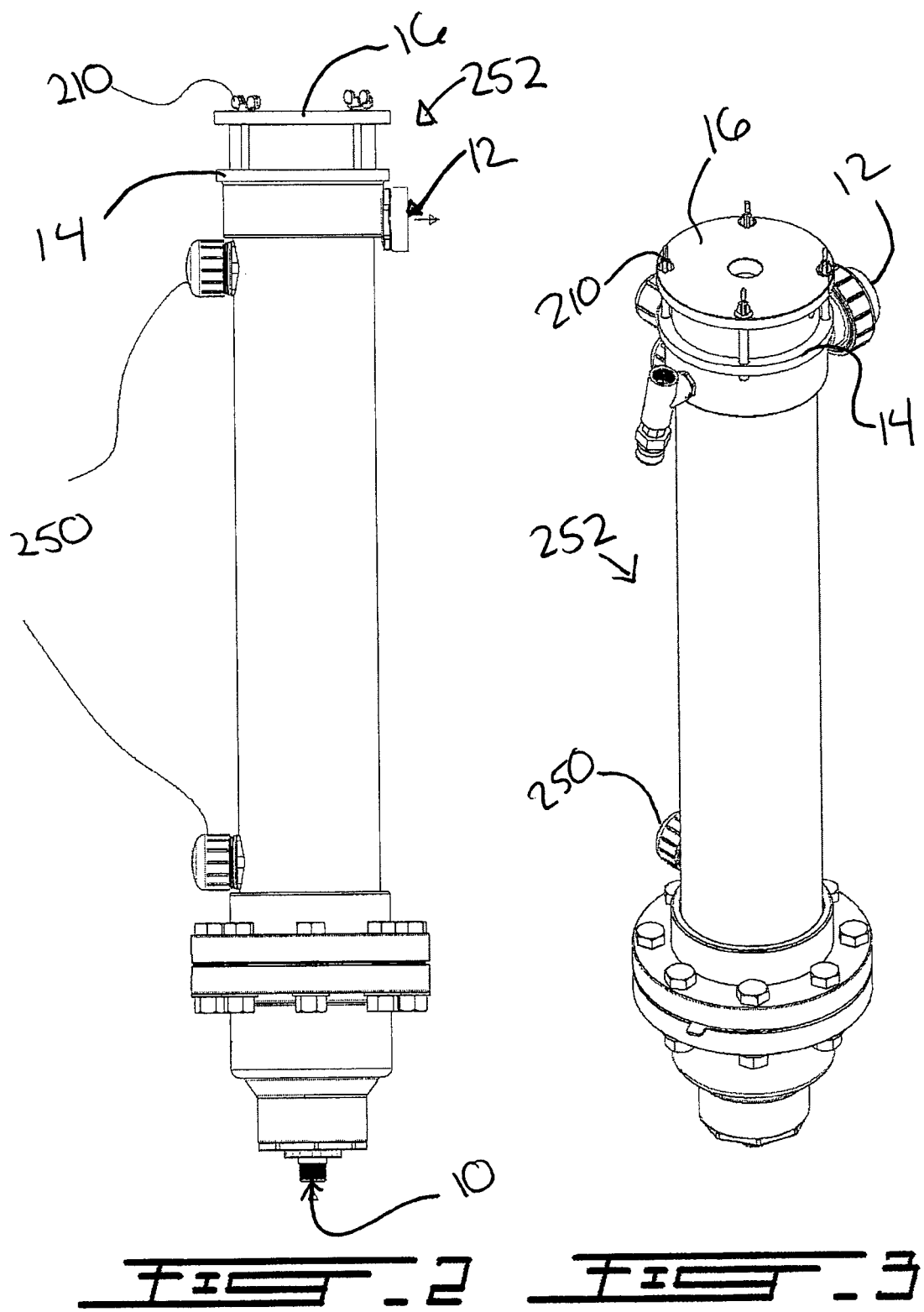

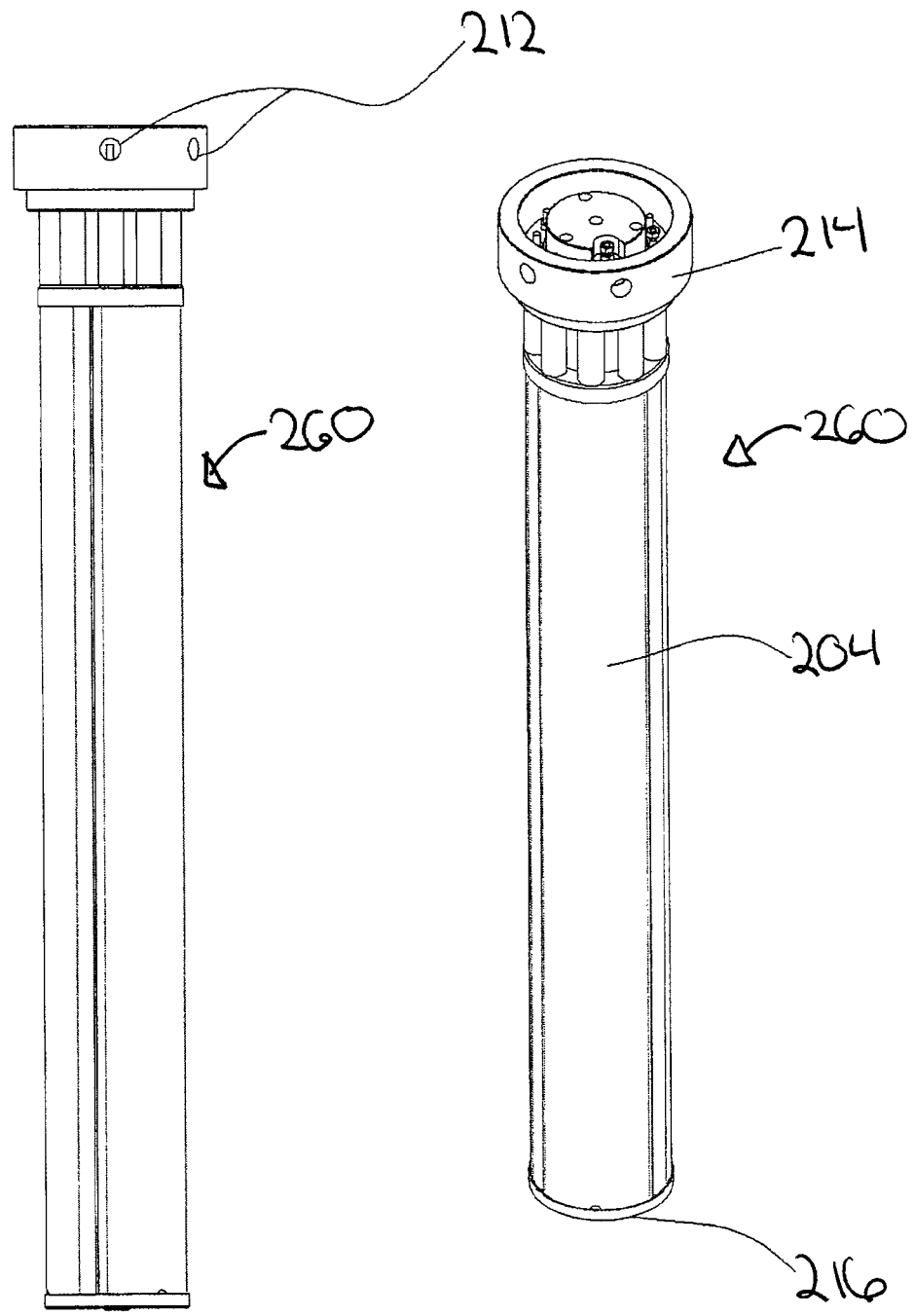

APPARATUS AND METHOD FOR HARVESTING AND DEWATERING OF MICROALGAE BIOMASS

CROSS-REFERENCE TO RELATED APPLICATIONS

The present patent application claims the benefits of priority of U.S. Provisional Patent Application No. 61/706,917, entitled APPARATUS AND METHOD FOR HARVESTING AND DEWATERING ALGAL BIOMASS, and filed on Sep. 28, 2012, at the United States Patent and Trademark Office, the content of which is hereby incorporated by reference in its entirety.

FIELD OF THE INVENTION

The present invention generally relates to a method and system for removing contaminants from wastewater using electrolysis, and more particularly to an electrolysis method and system that may be used for harvesting and for dewatering microalgae biomass, as well as extracting contents from microalgae.

BACKGROUND OF THE INVENTION

Sustainable development focuses on operational efficiency while promoting the minimization of environmental, social and economic impacts, demands a better utilization of our natural resources, especially the non-renewable ones. It is evident that the continued use of fossil fuels is no longer viable due to the depletion of global resources (Brennan and Owende, 2009). A promising solution to energy supply in the long-run is biofuels, and particularly those produced from microalgae. In addition to offering a solution that minimizes climate change by reducing $CO_2$ emissions, which is ultimately achieved when the $CO_2$ is metabolized by the microalgae in their growth and reproduction cycle. Such processes are more particularly generated through photosynthesis. Furthermore, microalgae are a rich source of valuable amino acids, proteins, pigments, vitamins, and antioxidants. Accordingly, microalgae offer key advantages over traditional feed stocks, such as fast photosynthetic growth rates and high lipid content, which can ultimately be converted into biofuels. The energy efficiency of microalgae had been reported to be 30 to 100 times greater than the energy efficiency of terrestrial plants. Also, as other biofuel sources (e.g. corn or sugar cane) the culture of microalgae does not necessarily compete with food supply.

Today, microalgae harvesting and dewatering remains a major obstacle to industrial-scale production of biofuels (Pienkos Darzins, 2009; Uduman et al, 2010). Although, several technologies for the separation of microalgae biomass are known, they still require large capital investments and/or large operational expenditures. The challenge of cost-efficient harvesting and dewatering of microalgae resides in their small size and low concentration in the culture medium. Existing harvesting and dewatering technologies such as centrifugal recovery and filtration require a relatively high amount of energy. Therefore, there is an interest in finding innovative methods for harvesting and dewatering microalgae with lower capital expenses (CAPEX) and operational expenses (OPEX).

Electrocoagulation and/or electro-floatation can be a competitive way to perform harvesting and primary dewatering of microalgae biomass as they both allow the destabilization of the suspended microalgae, followed by their aggregation into settleable and/or floatable flocs. The negative charge at the surface of microalgae creates repulsive forces between negatively charged particles, which cause them to remain suspended in solution. These repulsive forces can be weakened and cancelled by adding cations into the solution and thus lowering the charge of the microalgae. Cations of magnesium can be injected into the solution by electrolysis using a sacrificial anode made of a magnesium-based alloy. Simultaneously, gas bubbles produced at the electrodes lift the flocs towards the exit of the reactor. Moreover, many species of microalgae have a natural tendency to float since their cells contain relatively large quantities of low density lipids, which accelerates the floatation process.

Extraction of microalgae cells contents may be done using electrocoagulation, through the electric fields that helps permeating the cellular membrane. Lysis of the microalgae is driven by the oxidation process and by hydroxyl radicals that are a by-product of electrocoagulation. Electrolysis produces various oxidants, including hydrogen peroxide, ozone, chlorine, and chlorine dioxide. This method can be performed without the use of toxic solvents and chemicals. In addition to this, recent studies have demonstrated that electrocoagulation could also be used to discolor molecules when this is desired, and again without the use of toxic solvents and chemicals.

Microalgae typically range in size from 1 to 100 µm and they behave similarly to colloidal particles. As previously mentioned, freshwater and marine species of microalgae can be destabilized by making attractive forces between particles greater than the naturally occurring repulsive forces amongst them. Overall, the stability of particles in solution results from the sum of attractive van der Waals forces and of electrostatic forces responsible for the repulsion of particles, as well of residual forces originating from the steric effect of solvent molecules.

Coagulation can be achieved by chemical or electrochemical means. Chemical coagulation has been successfully used for decades, but it has a few shortcomings, which include risks for health and safety posed by the handling of hazardous chemicals and costs associated with the handling and treatment of the generated sludge that may contain relatively high levels of heavy metals. Moreover, traditional coagulation and flocculation techniques may use chemicals that are proven to be less effective in saline conditions.

Although the principles at works in electrocoagulation resembles that of traditional coagulation, there are some key differences between the two processes. Flocs generated by electrocoagulation differ from those generated by chemical coagulation because they tend to contain less bound water and to be more easily filterable. Moreover, harvesting and primary dewatering of microalgae using the magnesium-based alloy anodes enables one to maintain the heavy metal concentrations, particularly for Al and Fe, below the desired levels. Regarding the steps of extracting of microalgae, electrocoagulation and electro-floatation eliminates the use of organic solvents.

Electrocoagulation generates flocs from suspended solids, which ultimately aggregate together to settle or float in a liquid/solid separation tank. Currents of ions and charged particles created by the electric field in the reactor promote collisions amongst ions and particles of opposite signs that migrate in opposite directions, leading to an electrolysis induced coagulation.

Electrolysis reactions taking place at the surface of the electrodes are accompanied by generation of micro bubbles of hydrogen at the cathode(s) and of oxygen at the anode(s).

These micro bubbles can further drive the upward movement of the microalgae flocs towards the exit of the reactor through floatation.

Applied electric current to a solution drives Faraday reactions at the interface between the electrodes and the treated solution, which leads to the establishment of chemical concentration gradients in the reactor. Depending on the design of the reactor and of the flow rate conditions in the reactor, a particular threshold of electro-kinetic energy can lead to the electrolysis of water, with the simultaneous development of pH gradients and with the transfer of electrolytic dissolution of the anode producing metal ions ($Mg^{2+}$, etc.) or cations of the electrolyte from the anode to the cathode. The main electrolysis reactions taking place in the reactor include the following:

At the cathode, the main reaction is:

$$4H_2O+4e^- \rightarrow 2H_2+4OH^- \quad \text{(Equation 1)}$$

The increase in hydroxyl ions can increase the precipitation of metal hydroxide. The pH of the cathode's region is basic. The following equations describe the chemical reactions at the anode:

$$2H_2O \rightarrow O_2+4H^++4e^- \quad \text{(Equation 2)}$$

If the anode is made of magnesium:

$$Mg \rightarrow Mg^{2+}+2e^- \quad \text{(Equation 3)}$$

There is a growing interest for electrocoagulation to be used to discolor molecules when this is desired without the use of toxic solvents and chemicals. It does so rather economically by eliminating the trace amounts of chlorophyll that are present in the microalgae cells while performing the treatment. Currently, this is mainly done using activated carbon or discoloration agents, which are both expensive techniques.

SUMMARY OF THE INVENTION

Separating microalgae from an aqueous solution remains a major hurdle to industrial-scale processing partly because of the small size of microalgae cells, thus the method of the present invention is highly relevant and of interest to this particular field. The core aspect of the present invention is to provide a method for harvesting and primary dewatering a microalgae solution to a dryness of about 3-5% using either or a combination of electrolysis processes of electrocoagulation and of electro-floatation.

According to one, yet non limitative embodiment of the present invention, a method for harvesting and primary dewatering a microalgae solution and/or extracting contents from microalgae cells using electrocoagulation module(s) containing quick loading magnesium-based alloy anodes and/or inert anodes cartridges is disclosed.

According to one, yet non limitative embodiment of the present invention, the method for harvesting and primary dewatering microalgae solution and/or extracting contents from microalgae cells using electrocoagulation and/or electro-floatation and/or a combination of both modules may be fed at a controlled flow rate to induce transition or turbulent flow regime inside the reactor(s).

According to one, yet non limitative embodiment of the present invention, the method for harvesting and primary dewatering microalgae solution and/or extracting contents from microalgae cells through electrocoagulation may comprise a magnesium-based alloy anodes that contain less than 10% of either Al or Fe.

According to one, yet non limitative embodiment of the present invention, the method for harvesting and primary dewatering microalgae solution and/or extracting contents from microalgae cells using a modular electrocoagulation and/or a modular electro-floatation and/or a modular system combining both technologies, may be quickly and easily installed and/or expanded over time.

According to one, yet non limitative embodiment of the present invention, the method for harvesting and primary dewatering microalgae solution and/or extracting contents from microalgae cells using electrocoagulation may comprise a quick loading anodes cartridge and cathode(s).

According to one, yet non limitative embodiment of the present invention, the method for harvesting and primary dewatering microalgae solution and/or extracting contents from microalgae cells using an electrocoagulation system may comprise a quick loading anodes cartridge and cathode(s) that can be easily replaced. The quick loading anodes cartridge should preferably be as easily replaceable as a membrane filter cartridge.

According to one, yet non limitative embodiment of the present invention, the method for harvesting and primary dewatering microalgae solution and/or extracting contents from microalgae cells using a modular electrocoagulation and/or a modular electro-floatation and/or a modular system combining both technologies, may comprise a rotating set of anode(s) as an option to add more kinetic energy into the solution to be treated.

According to one, yet non limitative embodiment of the present invention, the method for harvesting and primary dewatering microalgae solution and/or extracting contents from microalgae cells using electrocoagulation and/or a modular electro-floatation and/or a modular system combining both technologies, may employ anode module(s) with a plurality of anodes and of composition materials (ex: inert anodes and magnesium-based alloy anodes).

According to one, yet non limitative, embodiment of the present invention, the method for harvesting and primary dewatering microalgae solution and/or extracting contents from microalgae cells using electrocoagulation and/or a modular electro-floatation and/or a modular system combining both technologies, may comprise semi-cylindrical anode(s) module(s), which may be installed next to a cathode or between two cathodes in a concentric fashion.

According to one, yet non limitative, embodiment of the present invention, the method for harvesting and primary dewatering microalgae solution and/or extracting contents from microalgae cells using electrocoagulation and/or a modular electro-floatation and/or a modular system combining both technologies, may comprise a plurality of anodes having various geometries, such as but not limited to, semi-cylindrical, cylindrical, square, and conical, to react in combination with either one or two cathode(s) in order to coagulate and agglomerate the microalgae biomass.

According to one, yet non limitative embodiment of the present invention, the method for harvesting and primary dewatering microalgae solution and/or extracting contents from microalgae cells based on the principle of a sacrificial anode composed of a magnesium-based alloy, typically subjected to the application of a potential difference between the anodes and the cathode(s) is disclosed. The cathode(s) may be made of steel or of another metal or alloy identical to that of the anode. The application of a DC electrical current between the anodes and the cathode(s) produces a coagulant in situ and acts to form flocs and to agglomerate the microalgae biomass.

According to one, yet non limitative embodiment of the present invention, the method for harvesting and primary dewatering microalgae solution and/or extracting contents from microalgae cells using electrocoagulation and/or electro-floatation and/or a combination of both technologies, may comprise the option for a mechanical agitation of the anodes and/or establishment of a transition or turbulent flow rate in the reactor for sake of achieving an optimal performance.

Other and further aspects and advantages of the present invention will be obvious upon an understanding of the illustrative embodiments about to be described or will be indicated in the appended claims, and various advantages not referred to herein will occur to one skilled in the art upon employment of the invention in practice.

BRIEF DESCRIPTION OF THE DRAWINGS

Referring now to the drawings which form a part of this original disclosure:

FIG. 1 is a schematic illustration of a modular skid of electrolysis reactors in accordance with at least one embodiment of the invention;

FIG. 2 is a schematic illustration of the exterior view of an electrocoagulation reactor in accordance with at least one embodiment of the invention;

FIG. 3 is a perspective view of the exterior view of an electrocoagulation reactor of FIG. 2;

FIG. 6 is a schematic illustration of a quick loading anodes cartridge in accordance with at least one embodiment of the invention;

FIG. 7 is a perspective view of the exterior view of an electrocoagulation reactor of FIG. 6;

DETAILED DESCRIPTION OF THE PREFERRED EMBODIMENT

Figure 4:
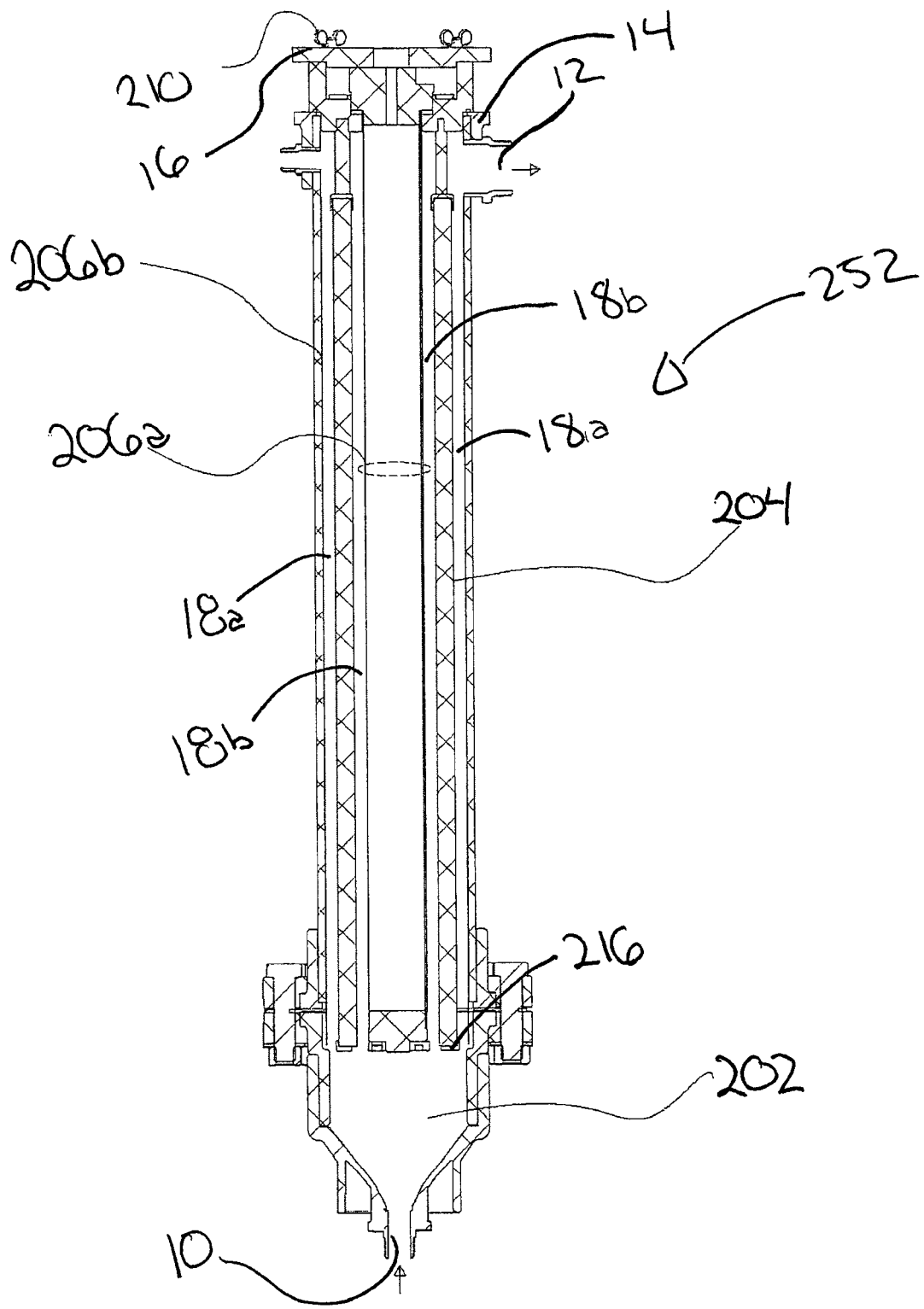
FIG. 4 is a schematic illustration of the interior view of an electrocoagulation reactor in accordance with at least one embodiment of the invention.

In the present embodiment, now referring to FIG. 1, a system comprising a plurality of electrocoagulation module is shown. In this embodiment, the plurality of reactors are arranged in a modular arrangement to make up an electrolysis skid. In this embodiment, four electrolysis reactors are arranged in a single skid that is connected to a single control panel, including a Programmable Logic Controller (PLC) and a Human Machine Interface (HMI). The number of reactors required for treatment of fluid, typically a microalgae solution, will be a function of the dosage that must be applied to the variety and concentration of microalgae to be harvested and dewatered. Moreover, the design may be optimized with respect to other process steps and with respect to the working conditions that are being used.

In another embodiment, a skid could potentially comprise 1, 2, 3, 4, 5, or even more reactors. Likewise, it is possible to have more than one skid depending on the extent of the treatment required by the fluid. Accordingly, multiple reactors and/or multiple skids could be installed to achieve the objectives of both microalgae harvesting and dewatering. The actual configuration of the reactors in each skid may also vary and is typically left to the discretion of the client, depending on specifications and constraints such as the available footprint.

The present invention also provides a method for separating, harvesting and primary dewatering microalgae biomass from a microalgae solution. The method comprises the steps of:
  (a) providing a vertical electrolysis reactor, said reactor comprising:
    a vertical tubular housing having a bottom and a top, and defining an electrocoagulation chamber extending from the top of the housing and a flow dispersion chamber located below the electrocoagulation chamber;
    an inlet adjacent to the bottom of the housing for injecting into the flow dispersion chamber a microalgae solution to be treated; and
    an outlet adjacent to the top of the housing and connected to the electrocoagulation chamber for extracting the solution from the reactor;
    wherein the electrocoagulation chamber comprises at least one anode and at least one cathode electrically connected together to perform electrolysis of the microalgae solution inside the electrocoagulation chamber; and
    wherein the at least one anode and the at least one cathode are substantially concentric one about the other and substantially parallel to a flow of the microalgae solution;
  (b) pumping the microalgae solution into the reactor via the inlet to create a flow of the solution from the bottom to the top of the reactor where the solution exits the reactor via the outlet;
  (c) varying a rate of the flow rate when said microalgae solution is injected into the electrolysis reactor so as to create turbulences in the microalgae solution inside the electrolysis reactor;
  (d) routing the turbulently injected microalgae solution in the electrolysis reactor from the bottom of the electrolysis reactor to the top thereof;
  (e) applying an electric current between the at least one anode and the at least one cathode while the microalgae solution flows through the electrocoagulation chamber for aggregating microalgae components of the solution to form flocs in the microalgae solution;
  (f) re-injecting the solution that exits the reactor via the outlet at the top of the reactor into the same reactor via the inlet at the bottom of the reactor; and
  (g) repeating steps (c) to (f) for multiple passes through the reactor until treatment is completed.

The present invention also provides a system for separating, harvesting and primary dewatering microalgae from a microalgae solution. The system comprises:
  a vertical electrolysis reactor comprising:
    a vertical tubular housing having a bottom and a top, and defining an electrocoagulation chamber extending from the top of the housing and a flow dispersion chamber located below the electrocoagulation chamber;

an inlet adjacent to the bottom of the housing for injecting into the flow dispersion chamber a microalgae solution to be treated;

an outlet adjacent to the top of the housing and connected to the electrocoagulation chamber for extracting the solution from the reactor; and at least one anode and at least one cathode electrically located inside the electrocoagulation chamber and connected together to perform electrolysis of the microalgae solution inside the electrocoagulation chamber while the microalgae solution flows through the electrocoagulation chamber for aggregating microalgae components of the solution to form flocs in the microalgae solution; the at least one anode and the at least one cathode being substantially concentric one about the other and substantially parallel to a flow of the microalgae solution created between the bottom to the top of the reactor when the solution is injected into the reactor;

a feed pump operatively connected to the inlet for injecting the microalgae into the electrolysis reactor;

a first valve configured to automatically control and modulate the feed pump for varying a rate of the flow rate when said microalgae solution is injected into the reactor so as to create turbulences in the microalgae solution inside the electrolysis reactor;

a recirculation loop operatively connecting the outlet to the inlet for re-injecting the solution that exits the reactor via the outlet at the top of the reactor into the same reactor via the inlet at the bottom of the reactor allowing multiple passes through the reactor until treatment is completed; and a second valve operatively connected to the recirculation loop for extracting the solution from the loop once the solution is treated.

In the present embodiment, now referring to FIGS. 2 and 3, the exterior of an electrolysis reactor is shown. The electrolysis reactor typically comprise an inlet 10, two locations for high temperature switches 250, an outlet 12, and a top member 14, the top member or crown 14 is generally sealed by a cover plate 16 that is secured using fasteners 210 such as quick-tightening bolts.

According to an embodiment to the present invention, the two high temperature switches 250, one at the top and one at the bottom of the reactor 252, are generally used to prevent overheating of the electrolysis reactors 252 in no-flow or in low-flow conditions. The high temperature switches 250 are generally connected to a security relay installed in the control panel. In the event that one of the high temperature switches 250 is activated due to a rise in temperature in the reactor 252 beyond a pre-defined temperature setting, the security relay shall turn off the system and the corresponding DC power supply in order to prevent the overheating of the reactor 252.

Still referring to FIGS. 2 and 3, the reactor 252 is preferably fed from the bottom of the reactor, and using a turbulent or transition type of flow rate in order to insure a continuous cleaning of the anode(s) 204 and cathode(s) 206. The high temperature switches 250 are preferably used to trigger a critical alarm in the control panel whenever the temperature inside the reactor 252 reaches a pre-determined threshold. Such increase in temperature may occur if the power supply is 'ON' while the flow is stopped over a prolonged period of time. The outlet 12 of the reactor 252 is generally located near the top of the reactor 252 preferably above the top of the anodes 204 (see FIG. 4), at a height passed the reactive zone 18a, 18b of the reactor 252 that is comprised between the anode(s) 204 and the cathode(s) 206a, 206b.

In the present embodiment, now referring to FIG. 4, the interior of an electrolysis reactor is shown. Above the inlet port 10 at the bottom of the reactor 252 is generally a flow dispersion chamber 202 that helps distributing the rising flow in an evenly fashion throughout the cross-sectional area between the anode(s) 204 and the cathode(s) 206a, 206b. Such a configuration is desired to make sure the fluid is forced through the reactive areas 18a, 18b. As such, the only way for the fluid to make its way out of the reactor is by passing through the reactive zone 18a, 18b of the reactor thereby being subjected to the electrolysis reaction. In such a configuration, no bypass is possible. Consequently, this configuration ensures that all the fluid is exposed to the electrolysis treatment.

Figure 5:
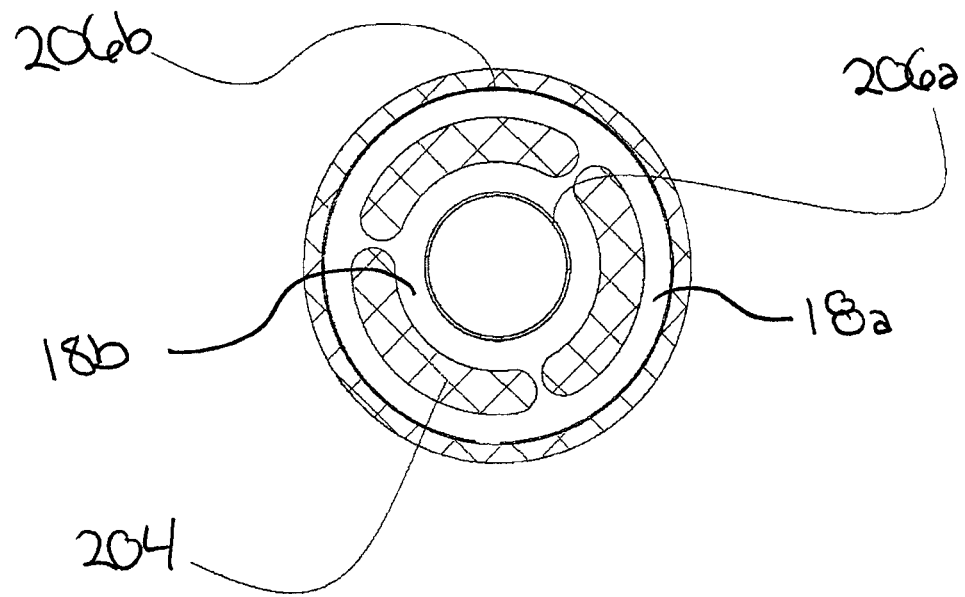
FIG. 5 is a schematic illustration of the typical concentric arrangement of anodes and cathodes in an electrolysis reactor in accordance with at least one embodiment of the invention.

In the present embodiment, now referring to FIG. 5, the three (3) semi-circular anodes 204 are generally sandwiched between an inner cathode 206a and an outer cathode 206b. The gap 18a-18b between the anodes 204 and cathodes 206a, 206b is where the fluid is allowed to pass, and where it serves as a conductor between the two types of electrodes, thus allowing for the electrolysis treatment to occur. This concentric arrangement between anodes 204 and cathodes 206a, 206b is typical of this electrolysis method.

In another embodiment, the reactor could have a single cathode or cathode layer and a single anode and anode layer. In such an embodiment, the width of the gap between the anodes and the cathode could be controlled by using a polarity reversal, thus allowing the electrodes to act as either the anode or the cathode upon reversal of the polarity. In such an embodiment, the width of the gap between the electrodes would typically be controlled using the polarity reversal feature. Similarly, in such an embodiment, a controlled reversal of polarity may be applied to compensate for the consumption of the anodes over time. For instance, in an embodiment where the reactor comprises two layers of electrodes that can be switched to being either anodes or cathodes, and the outer layer has an overall mass of 15 kg of reactive metal while the inner layer only has a 9 kg mass of magnesium-based alloy. Therefore, to replace the quick-loading cartridge at an optimal time, it is best to use up the outer layer at a rate that is 5/3 times faster than that of the inner layer in order to end up with a more even consumption of the electrodes of different size and mass. The polarity reversal would thus be used to direct the electrode to a surface ratio between the anode and the cathode approximating 1. As such, once the desired surface ratio has been obtained, the polarity reversal would be used in an attempt to maintain such a desired surface ratio between the anodes 204 and the cathode near constant value. As such, the cathode may play the role of an anode for a determined amount of time, and then be switched back to being a cathode again, once the anode/cathode surface ratio is re-established.

In the present embodiment, still referring to FIG. 5, the electrocoagulation system has a concentric arrangement of the three (3) semi-cylindrical anodes that are typically sandwiched between an inner cathode 206a and an outer cathode 206b. Again, the gap 18a, 18b between the anodes 204 and cathodes 206a, 206b is where fluid is allowed to pass, and where it serves as a conductor between the two types of electrodes, thus allowing for the electrolysis treatment to happen. In other words, any gap 18a, 18b between the cathode 206a, 206b and anode(s) 204 inside the reactor is where the fluid may pass on its way up towards the outlet. A summation of all the gap 18a, 18b areas or reactive areas yields the cross-sectional area of passage that is used to determine the flow rate required to establish a transition or turbulent flow regime inside the reactor. As previously mentioned, this concentric arrangement between anodes 204 and cathodes 206 is typical of this electrolysis method, although another design proposes to have only one cathode 206 and to control the width of the gap between the anodes 204 and the cathode 206.

Now referring to FIGS. 6 and 7, in the present embodiment, a quick-loading electrode replacement cartridge 260 typically inserted into the body of the reactor 252. When the anodes 204 are close to being used up as indicated by a special function programmed in the PLC and transmitted to the HMI, the operator may replace the used cartridge 260 with a new one. The method offers a configuration that allow a quick and simple maintenance operation. The only steps required by operator to change the cartridge 260 first unscrew the fasteners 210, typically bolts, securing the cover plate 16 and remove the used cartridge 260, with or without the use of a hoist. It is to be noted that the use of the hoist will depend on the type of reactor 252 being serviced and the weight and size of the cartridge 260. The operator subsequently insert a new cartridge 260 into the reactor 252 and replace the cover plate 16 and the fasteners 210. The quick-loading electrode replacement cartridge 260 is to be lifted by the crown onto which the anode(s) 204 and cathode(s) 206a, 206b are fixed by another set of fasteners, typically screws.

According to an embodiment to the present invention, the replacement of sacrificial anodes 204 may be achieved using a quick-loading electrode cartridge 260. The innovative design of the present system enables a quick replacement of the anodes 204 and an ease of assembly of the reactor 252. Electrode cartridges 260 are typically provided as pre-assembled electrodes. Furthermore, they are designed to smoothly slide down the reactor 252 following the insertion of the lower part of the cartridge 260 from the top of the reactor 252. Guiding parts preferably installed along the walls and on the bottom of the reactor generally allow the operator to slide the electrode cartridge 260 down with ease. By using such a configuration, a proper alignment of the anodes 204 with respect to the cathode(s) 206 is generally ensured. Consequently, the DC may be distributed evenly throughout the reactor 252. Furthermore, ensuring proper alignment of the anodes with respect to the cathode(s) allows homogeneous consumption of the anodes, while maintaining a safe electromagnetic field between the electrodes.

A lift ring typically allows the cartridge 260 to be handled by a hook chained to a hoist, which can be used when the overall weight of the cartridge 260 exceeds a comfortable lifting weight for the operator (ex: more than 25 kg). The quick-loading electrodes replacement cartridge can be inserted rapidly into the reactor 252 since the lower guiding disk 216 and interior design of the body of the reactor 252 helps position the cartridge 260 correctly, without the need for manual adjustments or measurements. The hoist may be manual or electric, and installed on a rail or beam over the modular reactors 252 skid system thereby enabling a safe and easy lift of the spent electrode cartridge 260, and an easy lowering of the new electrode cartridge 260.

Moreover, electrical connections 212 for the DC power supply to the electrical distribution rings (one for the cathodes and one for the anodes) are generally made at the top or the reactor, through a pair of circular holes that are drilled into the water-tight crown 214. The electrolysis reactors 252 are supplied with DC coming from variable voltage and amperage DC power supplies. The DC power supplies are generally monitored and controlled by a PLC to ensure a smooth operation of this fully automated system.

Figure 8:
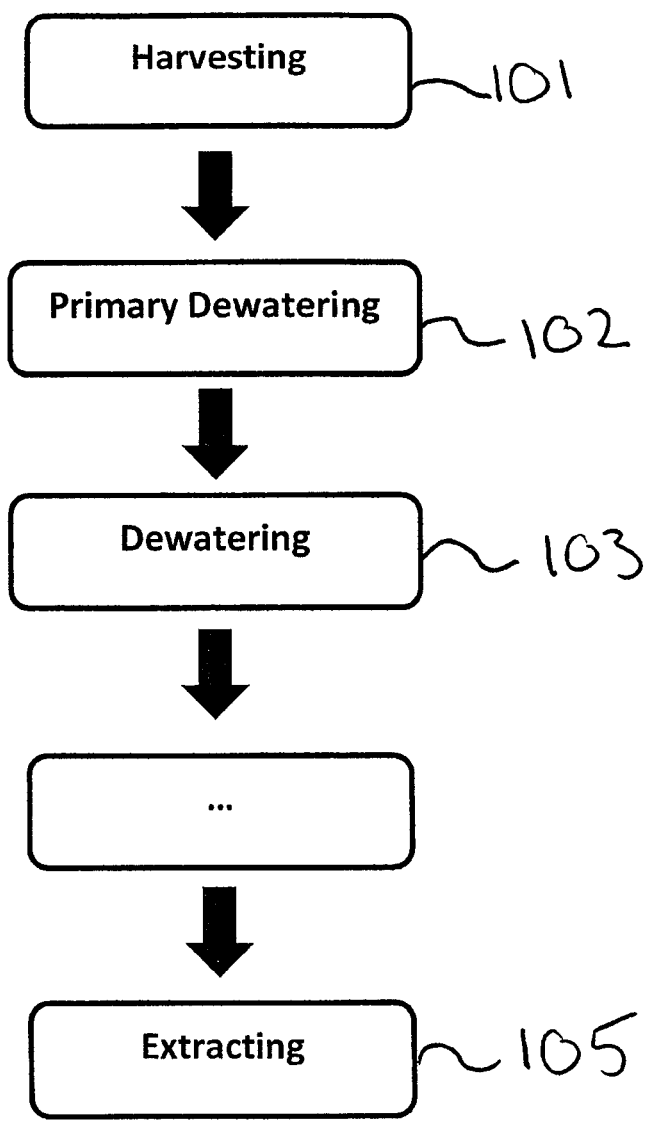
FIG. 8 is a schematic illustration of process steps where the proposed method can be used in accordance with at least one embodiment of the invention.

In one embodiment, now referring to FIG. 8, a series of steps comprised in the harvesting and primary dewatering of a microalgae solution is shown. The method may be used for harvesting 101, primary dewatering 102, and eventually dewatering 103 and extracting 105 the microalgae biomass from the microalgae solution. It may also be used to extract specific compounds of value contained within the microalgae cells. These processes in the present method may be used competitively, as depicted FIG. 8. The method in accordance with the present invention may be used on its own or in combination with other technologies. The electrolysis method can thus be applied for harvesting 101, primary dewatering 102, and extracting 105 targeted microalgae contents such as lipids which generally have a much lower density than water and can be extracted as floatables at the surface of the liquid/solid separation tank once the algal solution has been subjected to the treatment. Once harvested lipids contained inside vacuoles of microalgae cells can be further processed and transformed into biofuel. As far as dewatering is concerned, the method may be used to feed a centrifuge that would further dry up the microalgae, up to a practical level for processing and transportation. It is believed that combining the present electrolysis system with a centrifuge in the dewatering step would make the whole process more economical, and thus more attractive to the industry. Primary dewatering 102 performed by the electrolysis system would help increase the dryness of the harvested microalgae up to an optimal concentration of the feed to a centrifuge or any other dewatering technology, as shown in the process steps of 103 (FIG. 8), 117 (FIG. 9), and 127 (FIG. 10).

Now referring to FIGS. 8-11, whenever needed, the recirculation loop through the electrolysis reactors can include the liquid/solid separation tank 54. As such, the fluid coming out of the outlet 36 of the liquid/solid separation tank would be collected and pumped back to the inlet of the electrolysis reactors 252 to undergo another pass, and be repeated until treatment is completed.

Figure 11:
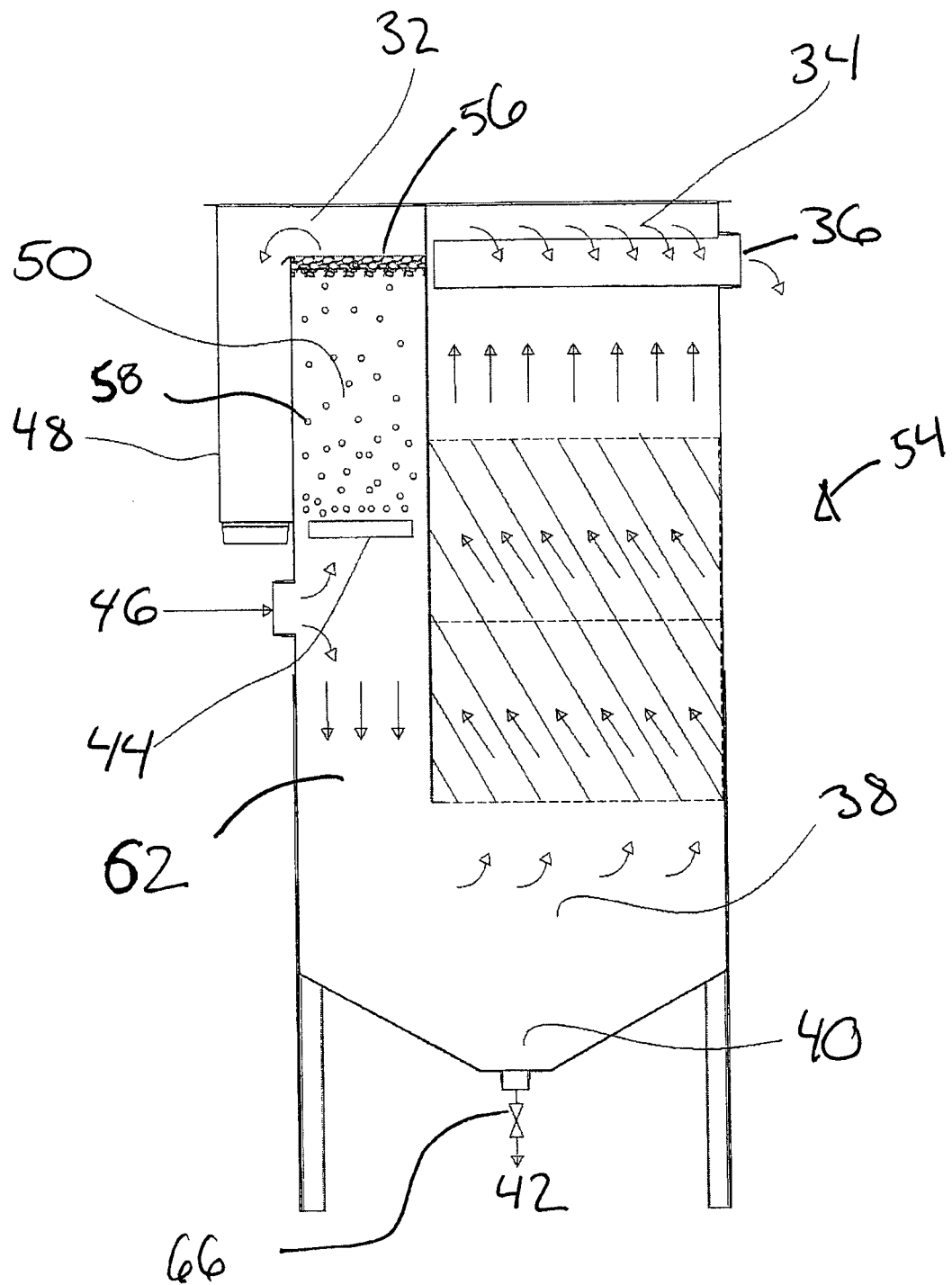
FIG. 11 is a schematic illustration of the inside view of the liquid/solid separation tank featuring a floatation section and a settling section in accordance with at least one embodiment of the invention.

In one embodiment, now referring to FIG. 11, the interior of a liquid/solid separation tank especially designed to optimize the separation of flocs produced by the electrolysis reactor(s) 252 is shown. Once the electrolysis treatment has been completed, automated valves may be opened and closed so that the fluid can be directed to the inlet 46 of the liquid/solid separation tank 54. At the inlet 46, the fluid enters a floatation section 50 where low-density flocs may generally be separated by rising up to the surface 56. Such a process may be optimized, when suitable, by the injection of micro bubbles 58 through a set of compressed air diffusers 44 installed just above the inlet 46 port. Once at the surface 56, the floating flocs build up and eventually fall off the weir 32, into a floatables collection box 48 where they can be harvested for further processing. Heavier flocs and the fluid generally sink towards the bottom of the floatation section 62 and arrive in the settling section 38 of the liquid/solid separation tank 54. Heavier flocs agglomerate to other flocs already present that have started to form a sludge blanket and accumulate in the sludge thickening area 40. The static weight of the column of water (ex: 2 m) over the sludge helps to compress it and to initiate the thickening of the sludge. Depending on the type of fluid treated and other operating conditions, an automated valve enables the operator to flush a fraction of the pre-thickened sludge whenever necessary. This sludge can then be sent to another process step for further dewatering. A set of lamella packs contributes to increase the settling rate of the flocs, i.e. to increase the flow rate through the liquid/solid separation tank by lowering the maximum fluid velocity and hydraulic residence time requirements. The fluid free from flocs can be collected at the top of the settling section of the tank through a set of clarified water collection troughs 34 installed on top of the lamella packs directing the water towards the outlet 36. The heavy flocs that have been pre-dewatered and that have accumulated at the bottom of the settling section of the liquid/solid separation tank can be extracted by opening the sludge valve 66 as show on number 42 of FIG. 11.

Various instruments may be installed in the system in order to monitor or control process parameters, such as pH, temperature, conductivity, and turbidity. Likewise, a multi-wavelength fluorometer can be added to the system in order to detect and measure the concentration of molecules of interest throughout the treatment steps.

According to an embodiment of the present invention, the design may perform efficiently for treating solutions characterized by a relatively wide range of conductivity values. Design optimization of the reactor, such as the use of more than one cathode, the use of a larger useful anode area, or the use of a tighter inter-electrodes gap can gear the reactor for treatment in a lower conductivity fluid. This demonstrates that this method is flexible enough to be suited for harvesting and primary dewatering varieties of microalgae that grow best in fresh water, brackish water, or salt water environment.

The anodes are preferably made of a magnesium-based alloy to enable the safe harvesting, primary dewatering, and extracting of microalgae without a substantial addition of undesirable metals like Al and Fe. This important aspect of the invention allows one to perform treatment without any material risk of contamination or any substantial loss in overall product quality.

According to an embodiment to the present invention, a programmed application loaded into the PLC allows the operator to visualize at any time the remaining mass of the anodes 204 on the HMI. In addition to being displayed on the HMI, the estimated remaining mass of the anodes 204 may be monitored and be plotted to be tracked over time so that the operator may anticipate and plan the optimal timing for the replacement of the anodes 204.

According to an embodiment to the present invention, the treated solution by the electrolysis system may be directed towards a floatation and settling tank that typically enables the efficient recovery of flocculated microalgae cells. The fluid first enters the tank in the floatation section that allows floating particles to be collected at the top of the tank through the overflow box. After hitting the separation plate that acts like a baffle, the fluid flows downwards towards the sludge collecting bottom. Heavier particles can settle and accumulate in this section of the tank, located under a set of lamellae pack modules. The rest of the fluid can move up through the lamellae channels and flow up towards the clarified water troughs that are installed at the top of the liquid/solid separation tank.

According to an embodiment of the present invention, compressed air may be injected into the floatation section of the liquid/solid separation tank in order to boost the performance. This can be achieved through tubular or plate diffusers that split the compressed air into micro bubbles. Micro bubble diffusers may be installed in order to cover a wide area over the floatation section of the liquid/solid separation tank, and at a specific height that optimizes the even distribution of micro bubbles across the cross-sectional area of the floatation section, considering that micro bubbles are likely to expand in size as they rise towards the surface.

Figure 9:
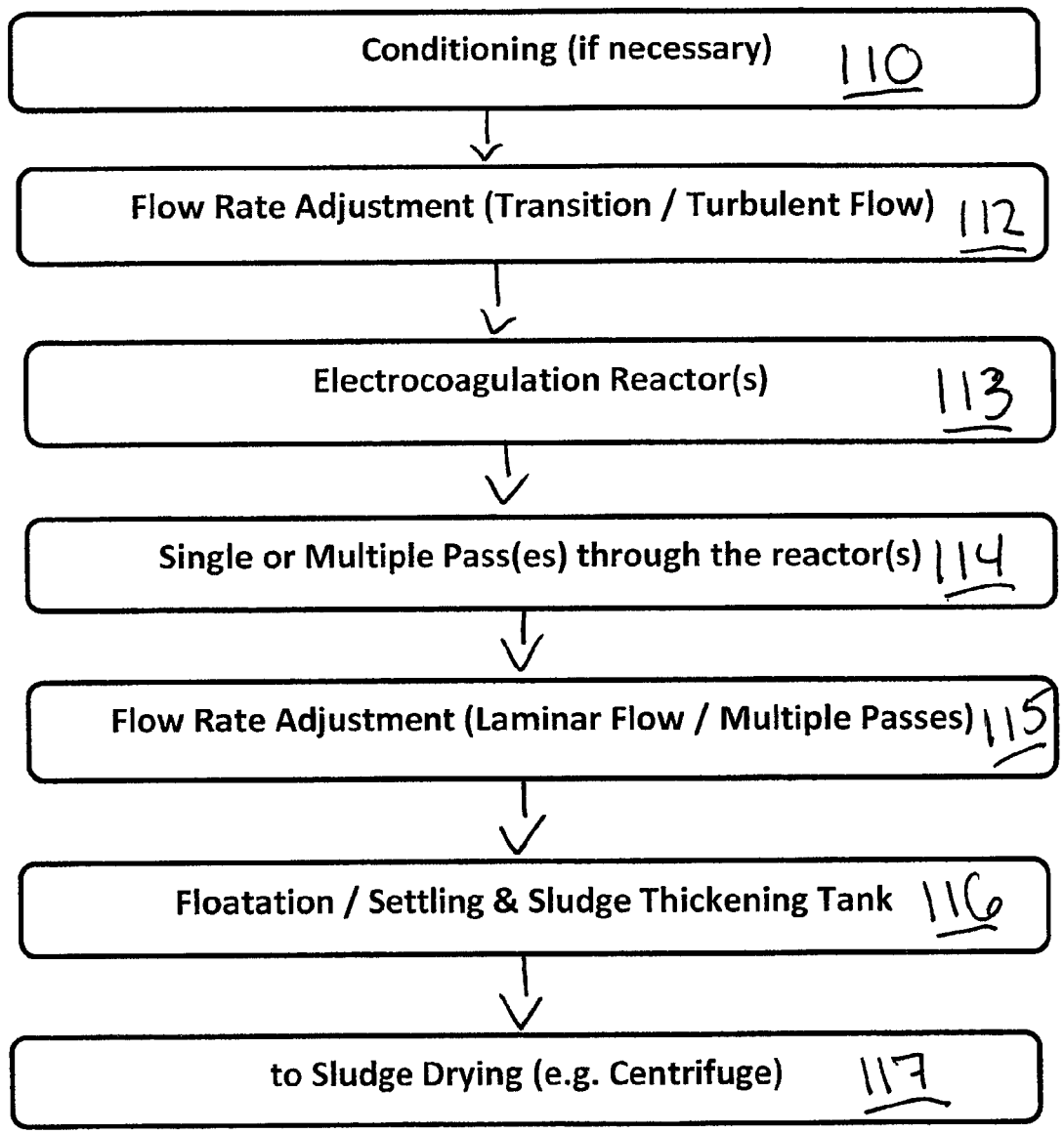
FIG. 9 is an illustrative flow chart showing an exemplary series of steps for the electrocoagulation process in accordance with at least one embodiment of the invention.
Figure 10:
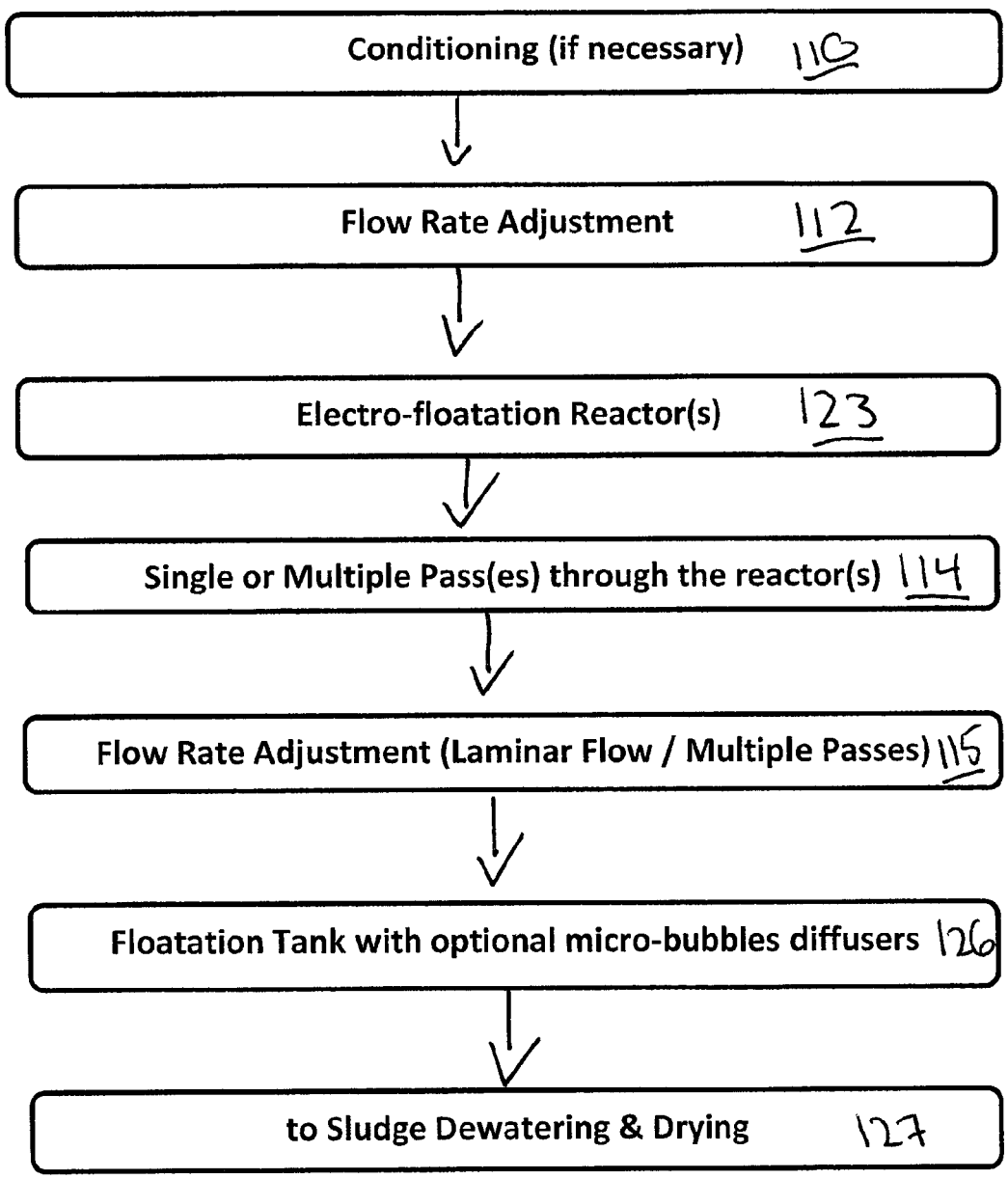
FIG. 10 is an illustrative flow chart showing an exemplary series of steps for the electro-floatation process in accordance with at least one embodiment of the invention.

According to one embodiment of the present invention, now referring to FIG. 9 the method comprises the steps of conditioning the microalgae solution 110 where such a step is necessary, including the adjustment of the flow rate to be of transition or turbulent regime 112, and then of directing the fluid into the electrocoagulation reactor(s) 113, to be then subjecting the liquid exiting the reactor to subsequent passes through the reactor(s) 114, adjusting the flow for either a single or multiple passes through the electrolysis reactor(s) 115, and ultimately directing the fluid to a liquid/solid separation tank 116, and finally transferring the harvested and dewatered microalgae to final dewatering 117.

According to another embodiment of the present invention, now referring to FIG. 10 the method comprises the steps of conditioning the microalgae solution 110 where such a step is necessary, including the adjustment of the flow rate to be of transition or turbulent regime 112, and then of directing the fluid into the electro-flotation reactor(s) 123, to be then subjecting the liquid exiting the reactor to subsequent passes through the reactor(s) 114, adjusting the flow for either a single or multiple passes through the electrolysis reactor(s) 115, and ultimately directing the fluid to a liquid/solid separation tank 126, and finally transferring the harvested and dewatered microalgae to final dewatering 127.

Now referring to FIGS. 9 and 10, it may be found that conditioning the fluid may contribute to lower operating costs. For instance, it may be worthwhile to add chemicals to the fluid, or to cool or heat the fluid prior to treatment, although this is generally not required. The only significant difference between electrocoagulation and electro-floatation processes lies in the type of anodes used to perform the electrolysis treatment. The method of the present invention preferably uses magnesium-based alloy anodes for electro-coagulation and inert anodes for electro-floatation. The choice of performing treatment with a certain number of passes through the reactors may also be affected by the type of electrolysis performed, namely electrocoagulation versus electro-floatation.

Now referring to FIG. 11, the fluid coming out from the top of the reactor is generally directed towards a liquid/solid separation tank 54 generally comprising a floatation section 50, a settling section 38, and a sludge thickening area 40. The fluid entering the liquid/solid separation tank 54 is first separated in the floatation section 50 where the low-density particles can rise to the surface 56, and in some cases be helped by the addition of micro bubbles diffusers 44 installed above the tank entry 46. The fluid then flows into the settling section 38 of the liquid/solid separation tank 54 where heavier particles sediment to the bottom and are compressed into a thicker sludge by the static pressure of the water column. Clarified water is collected by a series of troughs 34 installed at the surface of the tank, on top of a set of lamellae packs. The sludge can be extracted from the liquid/solid separation tank by opening the valve 66 located at the bottom of the settling area that is shaped like an inverted cone.

The method of electrolysis could be performed in a single pass or through multiple passes through the set of reactors. A set of automated ON/OFF valves may be used to direct the fluid in a loop so that it effectively passes multiple times through the set of reactors until the treatment is completed. The flow rate in the treatment loop and through the reactors may be controlled to optimize the treatment, and to maintain the optimal flow rate when performing electrolysis in the reactor. The flow rate in the treatment loop may also be adjusted by sizing the feed pump accordingly and through the use of an automatically controlled and modulating valve and the inlet of the feed line. Once the electrolysis treatment is completed, this modulating valve, as well as the other ON/OFF valves can be controlled to direct the fluid into the liquid/solid tank at a lower flow rate that is more conducive to floatation and settling. Again, the separation may be as floatables and/or as a settling sludge. The floatables and the settled sludge can be collected or harvested separately and further dried up using other dewatering technologies such as the centrifugation.

According to an embodiment to the present invention, the method uses the electrolysis system described herein in order to feed a liquid/solid separation tank, and then a dewatering unit (e.g. a centrifuge). A combination of the electrocoagulation and centrifugation systems would general allow the completion of the dewatering of the microalgae thus resulting in a drier final product. Furthermore, combining the electrolysis system with a centrifuge in the dewatering step could make the whole treatment process more economical. Accordingly, the primary dewatering performed by the electrolysis system would generally increase the dryness of the harvested microalgae up to an optimal concentration for the centrifuge to be fed, thus reduce high costs associated with the centrifugation.

According to an embodiment to the present invention, the method generally uses a flow control module in order to ensure that a transition or turbulent flow regime is maintained in the reactor throughout the treatment process. In addition, the type of flow regime will impact the collision rate in the fluid. The turbulent flow regime will generally promote the collision rate between ions and particles thereby increasing the kinetic energy of the fluid during electrolysis, while allowing to clean up the surface of the anode(s) and cathode(s) on a continuous basis.

According to an embodiment to the present invention the method allows the extraction of microalgae contents, such as lipids, using either electrocoagulation or electro-floatation technique or any combination thereof with an intensity that prevents damaging or deteriorating the targeted compounds.

According to one embodiment, the method for separating, harvesting and primary dewatering algal biomass from an algal solution described herein may be used as a cost-effective and efficient way to harvest and dewater microalgae, which may thrive in either freshwater, brackish water, or saltwater environments. The treatment of the liquid may be achieved using a single pass through the reactor(s) or may use a variety of techniques such as recirculation and/or multiple passes through reactor(s). The technique used will vary depending on the treatment objectives. As such, the intensity of the applied DC may be generally be adjusted to perform various treatment steps without altering targeted cell components or contents.

According to one embodiment, the method for separating, harvesting and primary dewatering microalgae biomass from a microalgae solution that typically comprises a feed tank equipped with level sensors and control instruments, a flow meter and an automated and modulating valve on the feed line, a modular set of electrolysis reactors fed from the bottom and each loaded with a quick replacement electrodes cartridge, which can be rapidly and easily loaded from the top of the electrolysis reactor. The reactor typically houses a set of cathode(s) and a plurality of anodes. Anodes and cathodes may be made from a similar or different compositions. The anodes for the electrocoagulation processes are preferably made from magnesium-based alloys as opposed to the anodes for the electro-flotation which are made from inert material.

According to an embodiment to the present invention, the method may be used as a primary dewatering process to generally bring the dryness of the harvested microalgae up to 3%, i.e. 1 kg of dry microalgae biomass associated with approximately 29 L of water.

According to an embodiment of the present invention, the present method may use different types of electrodes while still separating, harvesting and primary dewatering microalgae biomass from a microalgae solution. The design of the liquid/solid separation tank, for instance the injection of micro bubbles or not, may also be adapted to the variety or species of microalgae to be harvested and dewatered, or the nature of the compound to be collected.

According to an embodiment of the present invention, the method additionally comprise the option of adding multi-wavelength fluorometry allowing the detection in a more accurate manner and in a more precise manner the quantity and nature of molecules typically extracted from microalgae using the present electrolysis system. The sensor of the instrument may also be inserted on the clarified water line or at the surface of the liquid/solid separation tank.

While the invention has been described in connection with what is presently considered to be the most practical and preferred embodiments, it is to be understood that the invention is not to be limited to the disclosed embodiments and elements, but, to the contrary, is intended to cover various modifications, combinations of features, equivalent arrangements, and equivalent elements included within the spirit and scope of the appended claims. Furthermore, the dimensions of features of various components that may appear on the drawings are not meant to be limiting, and the size of the components therein can vary from the size that may be portrayed in the figures herein. Thus, it is intended that the present invention covers the modifications and variations of the invention, provided they come within the scope of the appended claims and their equivalents. Whenever needed, the recirculation loop through the electrolysis reactors can include the liquid/solid separation tank. This way, the fluid coming out of the outlet of the liquid/solid separation tank would be collected and pumped back to the inlet of the electrolysis reactors to undergo another pass, and this may be repeated until treatment if completed. Also, a number of semi-cylindrical anodes or electrodes different to three (3) could be used in any of the quick-loading electrodes cartridge.

The invention claimed is:

1. A method for separating, harvesting and primary dewatering microalgae biomass from a microalgae solution, the method comprising the steps of:
   (a) providing a vertical electrolysis reactor, said reactor comprising:
      a vertical tubular housing having a bottom and a top, and defining an electrocoagulation chamber extending from the top of the housing and a flow dispersion chamber located below the electrocoagulation chamber;
      an inlet adjacent to the bottom of the housing for injecting into the flow dispersion chamber a microalgae solution to be treated; and
      an outlet adjacent to the top of the housing and connected to the electrocoagulation chamber for extracting the solution from the reactor;

wherein the electrocoagulation chamber comprises at least one anode and at least one cathode electrically connected together to perform electrolysis of the microalgae solution inside the electrocoagulation chamber; and wherein the at least one anode and the at least one cathode are substantially concentric one about the other and substantially parallel to a flow of the microalgae solution;

(b) pumping the microalgae solution into the reactor via the inlet to create a flow of the solution from the bottom to the top of the reactor where the solution exits the reactor via the outlet;

(c) varying a rate of the flow rate when said microalgae solution is injected into the electrolysis reactor so as to create turbulences in the microalgae solution inside the electrolysis reactor;

(d) routing the turbulently injected microalgae solution in the electrolysis reactor from the bottom of the electrolysis reactor to the top thereof;

(e) applying an electric current between the at least one anode and the at least one cathode while the microalgae solution flows through the electrocoagulation chamber for aggregating microalgae components of the solution to form flocs in the microalgae solution;

(f) re-injecting the solution that exits the reactor via the outlet at the top of the reactor into the same reactor via the inlet at the bottom of the reactor; and (g) repeating steps (c) to (f) for multiple passes through the reactor until treatment is completed.

2. The method of claim 1, further comprising the step of:
electrically reversing the polarity of the at least one anode and at least one cathode in the electrocoagulation chamber for cleaning the electrodes and equalling consumption of the electrodes.

3. The method of claim 1, further comprising after step (g), the step of:

(h) separating the flocs from the microalgae by injecting the solution containing flocs into a liquid/solid separation tank configured to separate the flocs produced in the electrolysis reactor by floatation or by decantation.

4. The method of claim 3, further comprising after step (h), the following step:

(i) extracting the flocs floating at the surface/decanted at the bottom of the solution to form a sludge; and (j) dewatering the sludge by centrifugation.

5. The method of claim 1, wherein the at least one anode is made of a magnesium-based alloy comprising less than 10% of either Al or Fe.

6. The method of claim 5, wherein the at least one anode and the at least one cathode are integrated into a quick loading electrode cartridge.

7. The method of claim 6, wherein the quick loading electrode cartridge comprises a plurality of concentric semi-cylindrical anodes equally disposed circularly around located between two tubular cathodes in a concentric fashion.

8. A system for separating, harvesting and primary dewatering microalgae from a microalgae solution, the system comprising:

a vertical electrolysis reactor comprising:
a vertical tubular housing having a bottom and a top, and defining an electrocoagulation chamber extending from the top of the housing and a flow dispersion chamber located below the electrocoagulation chamber;

an inlet adjacent to the bottom of the housing for injecting into the flow dispersion chamber a microalgae solution to be treated;

an outlet adjacent to the top of the housing and connected to the electrocoagulation chamber for extracting the solution from the reactor; and at least one anode and at least one cathode electrically located inside the electrocoagulation chamber and connected together to perform electrolysis of the microalgae solution inside the electrocoagulation chamber while the microalgae solution flows through the electrocoagulation chamber for aggregating microalgae components of the solution to form flocs in the microalgae solution; the at least one anode and the at least one cathode being substantially concentric one about the other and substantially parallel to a flow of the microalgae solution created between the bottom to the top of the reactor when the solution is injected into the reactor;

a feed pump operatively connected to the inlet for injecting the microalgae into the electrolysis reactor;

a first valve configured to automatically control and modulate the feed pump for varying a rate of the flow rate when said microalgae solution is injected into the reactor so as to create turbulences in the microalgae solution inside the electrolysis reactor;

a recirculation loop operatively connecting the outlet to the inlet for re-injecting the solution that exits the reactor via the outlet at the top of the reactor into the same reactor via the inlet at the bottom of the reactor allowing multiple passes through the reactor until treatment is completed; and a second valve operatively connected to the recirculation loop for extracting the solution from the loop once the solution is treated.

9. The system of claim 8, wherein the at least one anode is made of a magnesium-based alloy comprising less than 10% of either Al or Fe.

10. The system of claim 8, wherein the at least one anode and the at least one cathode are integrated into a quick loading electrode cartridge comprising a plurality of concentric semi-cylindrical anodes equally disposed circularly around located between two tubular cathodes in a concentric fashion.

11. The system of claim 10, wherein the anodes are sacrificial anodes disposed in a semi-cylindrical manner.

12. The system of claim 11, wherein the anodes comprises at least two layers of sacrificial electrodes disposed in a semi-cylindrical manner.

13. The system of claim 8, further comprising a liquid/solid separation tank configured to separate the flocs produced in the electrolysis reactor by floatation/decantation, the tank being operatively connected to the valve for receiving the solution containing flocs from the reactor.

14. The system of claim 8, comprising a plurality of said vertical reactors in parallel configuration, wherein the inlet of a subsequent reactor is connected to the outlet of a precedent reactor, the last reactor of the system being connected to the inlet of the first reactor to form the loop.

* * * * *